United States Patent [19]

Chamberlin

[11] 4,374,993

[45] Feb. 22, 1983

[54] PROCESS FOR THE PREPARATION OF THE SULFATE SALT OF 2-AMINO-5-ALKYLTHIO-1,3,4-THIADIAZOLES

[75] Inventor: Kim S. Chamberlin, Kingsport, Tenn.

[73] Assignee: Eastman Kodak Company, Rochester, N.Y.

[21] Appl. No.: 271,323

[22] Filed: Jun. 8, 1981

[51] Int. Cl.$^3$ ............................................. C07D 285/12
[52] U.S. Cl. .................................................... 548/141
[58] Field of Search ....................................... 548/141

[56] References Cited

U.S. PATENT DOCUMENTS

| | | | |
|---|---|---|---|
| 2,759,947 | 8/1956 | Song et al. | 548/141 |
| 2,891,961 | 6/1959 | Turner et al. | 548/141 |
| 2,966,495 | 12/1960 | Song et al. | 548/141 |
| 3,033,901 | 5/1962 | Song | 548/141 |
| 3,657,215 | 4/1972 | Weaver et al. | 548/141 |
| 3,903,099 | 9/1975 | Rathgeb | 548/141 |
| 3,929,816 | 12/1975 | Rathgeb et al. | 548/141 |

FOREIGN PATENT DOCUMENTS 797469  7/1958  United Kingdom ............... 548/141

OTHER PUBLICATIONS

Bambas, Heterocyclic Compounds, pp. 143-153, (1952).
Elderfield; Heterocyclic Compounds, vol. 7, pp. 607-610, (1961).
Dala; Chem. Abs., vol. 53: 18947c, (1958).

*Primary Examiner*—Mary C. Lee
*Attorney, Agent, or Firm*—Gary C. Bailey; J. Frederick Thomsen; Daniel B. Reece, III

[57] ABSTRACT

Disclosed is a novel process for the preparation of the sulfate salt of 2-amino-5-alkylthio-1,3,4-thiadiazoles, which comprises reacting 2,5-dithiobiurea with a dialkylsulfate. Derivatives of compounds produced by this novel process are useful as chemical synthetic intermediates in the preparation of organic dyes and pharmaceuticals.

8 Claims, No Drawings

PROCESS FOR THE PREPARATION OF THE SULFATE SALT OF 2-AMINO-5-ALKYLTHIO-1,3,4-THIADIAZOLES

This invention concerns a novel process for the preparation of the sulfate salt of 2-amino-5-alkylthio-1,3,4-thiadiazoles.

The title compounds can be converted to their free amine which may then be used as intermediates in organic synthesis. They are particularly useful in the preparation of organic dyes [U.S. Pat. No. 3,657,215, "Thiadiazole Compounds and Textile Materials Dyed Therewith," (1972); U.K. Pat. No. 1,465,895, "Transfer Printing" (1977)] and in the preparation of pharmaceuticals such as sulfonamides [CA 78:72012p, "New Sulfonamide Derivatives of 1,3,4-Thiadiazole with Pharmacodynamic Activity" (1972)].

According to the process of this invention, the sulfate salt of 2-amino-5-alkylthio-1,3,4-thiadiazoles is prepared by adding a dialkylsulfate to a mixture of 2,5-dithiobiurea and water to obtain the sulfate salt of 2-amino-5-alkylthio-1,3,4-thiadiazoles. The resulting salt may be treated with base to produce the free amine which may then be used as a synthetic intermediate. The starting material, 2,5-dithiobiurea, is prepared by known procedures, for example, by reacting hydrazine with ammonium thiocyanate and acid followed by water washing.

By my novel process alkylation and cyclization of 2,5-dithiobiurea are achieved in one reaction process. It is also unique in that alkylation precedes ring closure of 2,5-dithiobiurea. This contrasts with previous procedures which require two separate reaction processes wherein ring closure of 2,5-dithiobiurea occurs prior to alkylation of the mercapto group. Prepared according to my new process the salt of 2-amino-5-alkylthio-1,3,4-thiadiazoles is obtained in good yield, in fewer steps and less overall reaction time than prior processes.

In the preparation of the title compounds, the mole ratio of dialkylsulfate to 2,5-dithiobiurea usually will be at least about 1.3:1. To achieve maximum yields of the desired compound the ratio is preferably from about 2.0–2.5:1. The alkylating agents most suitable for my process are the dialkylsulfates, of which dimethylsulfate and diethylsulfate are most preferred. Although higher esters such as dipropyl and dibutyl should also be effective their use is not favored because of economic restrictions.

The reaction is conveniently carried out in water. A weight ratio of at least 1 part water per part of dithiobiurea should normally be used while a weight ratio of about 3:1 is preferred, although satisfactory results are possible with larger amounts of water present. It is advantageous if a small amount of hypophosphorous acid is present in the water although good yields of the desired compound are obtained without the presence of the acid (about 77% assay yield). However, by conducting the reaction in the presence of the acid, the total yield may be increased to about 87% assay yield. The amount of hypophosphorous acid suitable is about 0.01 to 0.1 mole per mole of dithiobiurea with 0.05 mole being preferred for achieving maximum efficiency in the process.

The reaction process is preferably conducted at elevated temperatures, usually at about 90° C. to 105° C. (reflux). Normally, the mixture of water and dithiobiurea should be heated to about 90° C. to 105° C. prior to addition of the dialkylsulfate. To ensure optimum interaction between the dialkylsulfate and dithiobiurea, and to achieve maximum yields of the product compound, addition of the dialkylsulfate should be gradual or in increments. Under laboratory conditions, addition of the dialkylsulfate over a period of less than 30 minutes results in decreased yields of the product compound. When conducted on a larger scale, the minimum time required for addition of the dialkylsulfate will naturally increase due to the large volumes customarily dealt with commercially. Accordingly, the rate of addition is dependent upon the volume of reactants and the apparatus employed but should be at a rate which will achieve maximum product formation.

My novel process is further illustrated by the following examples.

EXAMPLE 1

A mixture of 150 g. 2,5-dithiobiurea, 5.0 g of 50% aqueous hypophosphorous acid and 500 ml of water was heated to reflux. Diethylsulfate (262 ml, 2.0 moles) was added over a period of one hour. The solution was refluxed for 5 hours and cooled to 5° C. Two moles of 50% NaOH was added keeping the temperature under 30° C. The white solid obtained was filtered and washed with 500 ml of ice-cold water. The total yield of 2-amino-5-ethylthio-1,3,4-thiadiazole was 162.2 g., 86.1% assay by HPLC, 87% assay yield.

EXAMPLE 2

The process as in Example 1 was carried out without the presence of the hypophosphorous acid using 37.5 g of 2,5-dithiobiurea, 125 ml of water and 82 ml (2.5 moles) diethyl sulfate. The total yield of 2-amino-5-ethylthio-1,3,4-thiadiazole was 55.1 g, 56.5% assay by HPLC, 77.3% assay yield.

The invention has been described in detail with particular reference to preferred embodiments thereof, but it will be understood that variations and modifications can be effected within the spirit and scope of the invention.

I claim:

1. Process for the preparation of a sulfate salt of a 2-amino-5-alkylthio-1,3,4-thiadiazole, which comprises adding a dialkylsulfate to a mixture of 2,5-dithiobiurea and water.

2. Process according to claim 1 wherein the mole ratio of dialkylsulfate to 2,5-dithiobiurea is at least about 1.3:1 and the weight ratio of water to dithiobiurea is at least about 1:1.

3. Process according to claim 1 wherein the mole ratio of dialkylsulfate to 2,5-dithiobiurea is about 2.0–2.5:1 and the weight ratio of water to dithiobiurea is about 3:1.

4. Process according to claim 2 or claim 3 wherein the dialkylsulfate is added to the mixture of 2,5-dithiobiurea and water at a rate which will achieve maximum product formation.

5. Process according to claim 4 wherein the mixture of 2,5-dithiobiurea and water contains about 0.01 to 0.05 moles of hypophosphorous acid per mole of dithiobiurea.

6. Process according to claim 5 wherein the dialkylsulfate is dimethylsulfate or diethylsulfate.

7. Process for the preparation of the sulfate salt of 2-amino-5-methylthio or ethylthio 1,3,4-thiadiazole which comprises adding dimethyl or diethylsulfate to a mixture of 2,5-dithiobiurea and water, wherein (1) the mole ratio of dimethyl or diethylsulfate to 2,5-dithiobiurea is about 2.0–2.5:1, (2) the weight ratio of water to 2,5-dithiobiurea is about 1.0–3.0:1, and (3) dimethyl or diethylsulfate is added to the mixture of 2,5-dithiobiurea and water at a rate which will achieve maximum product formation.

8. Process according to claim 7 wherein the mixture of 2,5-dithiobiurea and water contains about 0.01 to 0.05 moles of hypophosphorous acid per mole of dithiobiurea.

* * * * *